United States Patent
Garber et al.

(10) Patent No.: US 7,044,974 B2
(45) Date of Patent: May 16, 2006

(54) HIP PROSTHESIS WITH A MODULAR ACETABULAR CUP ASSEMBLY

(75) Inventors: Frank D. Garber, Pierceton, IN (US); John P. Hom, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 25 days.

(21) Appl. No.: 10/649,567

(22) Filed: Aug. 27, 2003

(65) Prior Publication Data

US 2005/0049713 A1    Mar. 3, 2005

(51) Int. Cl.
*A61F 2/32* (2006.01)

(52) U.S. Cl. .................. 623/22.21; 623/22.28

(58) Field of Classification Search ............ 623/22.21, 623/22.24–32, 22.36, 22.39–40
See application file for complete search history.

(56) References Cited

U.S. PATENT DOCUMENTS

| | | | | |
|---|---|---|---|---|
| 3,848,272 A | * | 11/1974 | Noiles ..................... | 623/23.22 |
| 4,004,300 A | * | 1/1977 | English .................... | 623/22.17 |
| 4,336,618 A | * | 6/1982 | Raab ....................... | 623/23.59 |
| 4,491,987 A | * | 1/1985 | Park ........................ | 623/23.59 |
| 4,563,778 A | * | 1/1986 | Roche et al. ............. | 623/22.38 |
| 4,681,589 A | | 7/1987 | Tronzo ..................... | 623/22 |
| 4,714,477 A | * | 12/1987 | Fichera et al. ........... | 623/22.19 |
| 4,728,335 A | * | 3/1988 | Jurgutis .................... | 623/23.23 |
| 4,770,661 A | | 9/1988 | Oh ............................ | 623/23 |
| 4,778,474 A | * | 10/1988 | Homsy .................... | 623/22.14 |
| 4,883,491 A | * | 11/1989 | Mallory et al. .......... | 623/22.31 |
| 4,919,674 A | * | 4/1990 | Schelhas .................. | 623/22.29 |
| 5,049,158 A | * | 9/1991 | Engelhardt et al. ...... | 623/22.25 |
| 5,405,392 A | | 4/1995 | Deckner .................. | 623/22 |
| 5,549,701 A | * | 8/1996 | Mikhail ................... | 623/22.21 |
| 5,658,338 A | * | 8/1997 | Tullos et al. ............. | 623/22.39 |
| 5,658,348 A | | 8/1997 | Rohr ........................ | 623/22 |
| 6,224,633 B1 | * | 5/2001 | Kalberer et al. ......... | 623/22.24 |
| 6,368,354 B1 | | 4/2002 | Burstein .................. | 623/22.28 |
| 6,811,569 B1 | * | 11/2004 | Afriat et al. ............. | 623/22.32 |
| 2003/0050703 A1 | * | 3/2003 | Harris et al. .............. | 623/22.2 |
| 2004/0225369 A1 | * | 11/2004 | Lakin et al. ............. | 623/22.15 |

FOREIGN PATENT DOCUMENTS

| | | |
|---|---|---|
| DE | 19901710 A | 7/2000 |
| EP | 0144588 A | 6/1985 |
| EP | 0242633 A | 10/1987 |
| EP | 077511 A | 8/1988 |
| EP | 0353171 A | 1/1990 |
| EP | 0358600 A | 3/1990 |
| EP | 0586335 A | 3/1994 |
| EP | 0688546 A | 12/1995 |
| FR | 2210909 A | 7/1974 |
| FR | 2287209 A | 3/1990 |
| WO | WO92/22265 A | 12/1992 |
| WO | WO95/8586 A | 7/1995 |

* cited by examiner

*Primary Examiner*—Eduardo C. Robert
*Assistant Examiner*—Annette Reimers
(74) *Attorney, Agent, or Firm*—Cary Reeves; Jonathan Feuchtwang

(57) ABSTRACT

An acetabular cup assembly includes a shell component, a liner component, and means for retaining the liner in the shell including a spherical profile thread spiraling around a portion of each of the shell and liner.

12 Claims, 2 Drawing Sheets

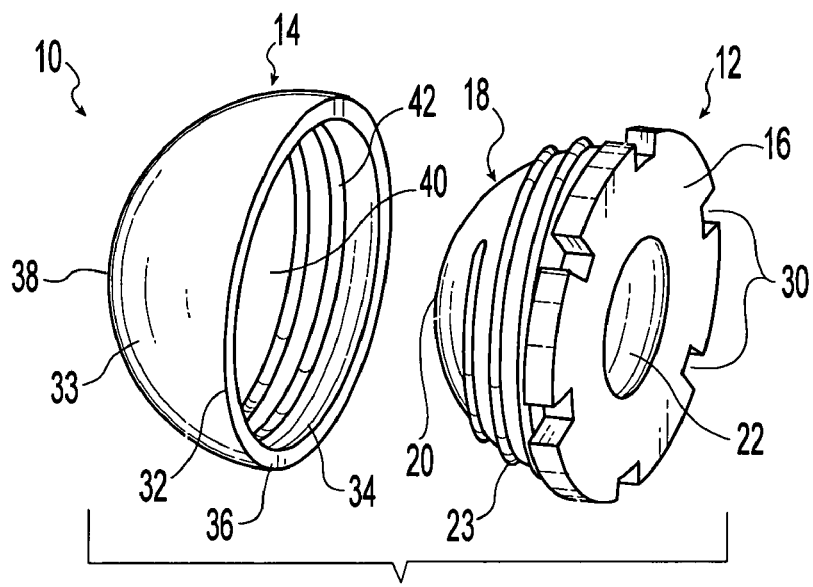
Fig. 1
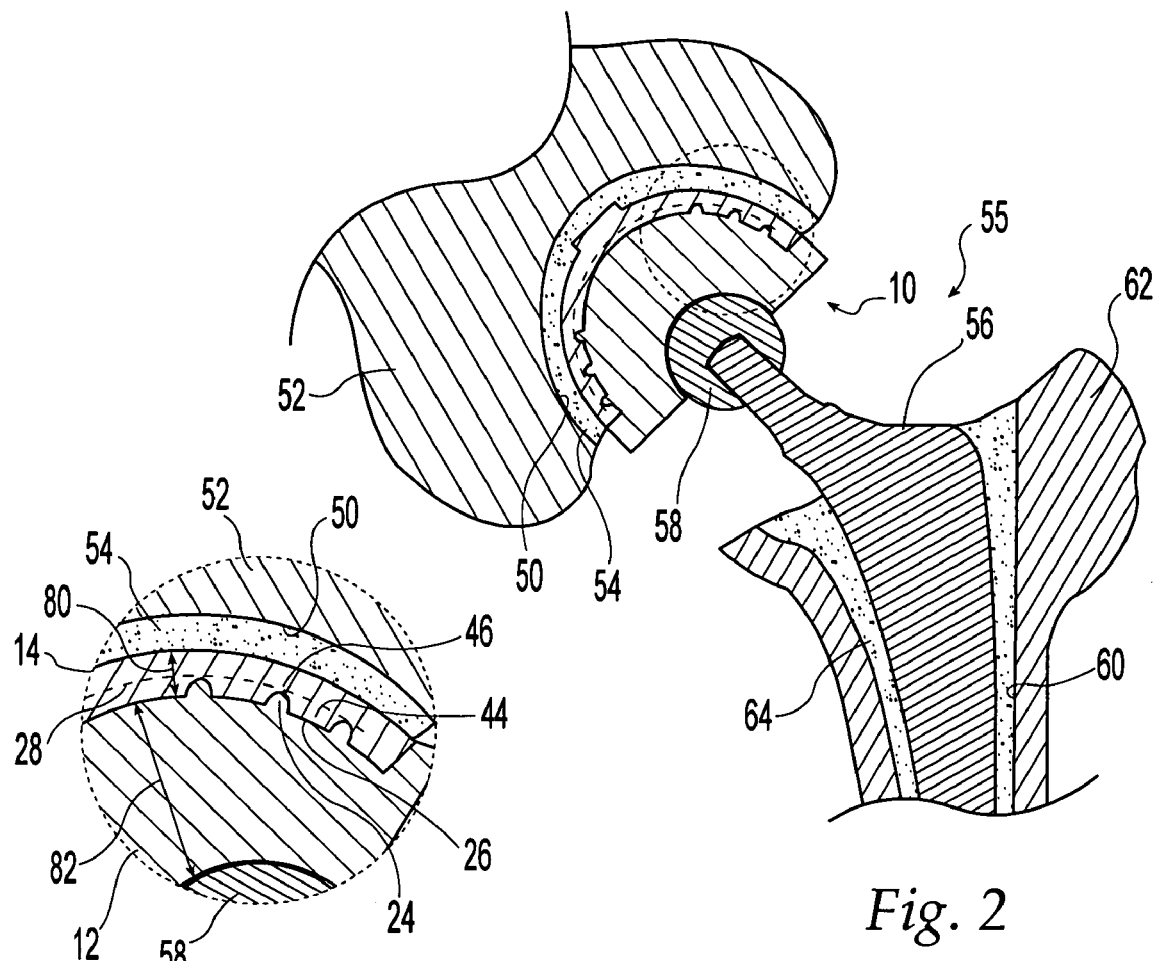
Fig. 2
Fig. 3

US 7,044,974 B2

HIP PROSTHESIS WITH A MODULAR ACETABULAR CUP ASSEMBLY

BACKGROUND

Total hip replacement surgery is commonly performed to alleviate pain and loss of function in injured and diseased hip joints. During this surgery, the articulating surfaces of the hip joint are replaced with prosthetic bearing components. The replacement components generally include a femoral component having a convex bearing surface and an acetabular cup component having a mating concave bearing surface.

Modular femoral and acetabular components have become popular because they allow the surgeon to assemble components in a variety of configurations at the time of surgery to meet specific patient needs relative to size and geometry. For example, modular femoral components generally include separate stem and head components that can be assembled in a variety of configurations of surface finish, stem diameter, stem length, proximal stem geometry, head diameter, and neck length. Likewise, modular acetabular components generally include separate shell and liner components that can be assembled in a variety of configurations of surface finish, shell outer diameter, liner inner diameter, and constraining fit with the femoral head. With a modular acetabular component, it is desirable to lock the shell and liner tightly together to minimize debris producing wear between them. It is also desirable to maintain a predetermined minimum liner thickness to prevent penetration of the liner by the femoral component.

SUMMARY

The present invention provides a hip prosthesis with a modular acetabular cup assembly.

In one aspect of the invention, an acetabular cup assembly includes a shell, a liner, and means for retaining the liner in the shell including a spherical profile thread spiraling around a portion of each of the shell and liner.

In another aspect of the invention, an acetabular cup assembly includes an acetabular liner and an acetabular shell. The acetabular liner has a generally hemispherical body with a substantially planar face on one side of the body and a convex back side opposite the face. The back side has a polar region. A concave bearing surface extends into the body through the face toward the polar region. The back side includes a liner screw thread having a liner thread root and a liner thread crest spiraling around the back side. The liner thread crest has a spherical profile. The acetabular shell includes a concave mating surface for receiving the liner. The concave mating surface includes a shell screw thread engageable with the liner screw thread.

In another aspect of the invention, a hip prosthesis system includes an acetabular liner with a thread having a spherical profile thread crest, an acetabular shell with a shell thread engageable with the liner thread, and a femoral prosthesis having a stem portion and a head portion. The head portion of the femoral prosthesis is matingly engageable with the liner concave bearing surface.

In another aspect of the invention, a method of making an acetabular cup assembly includes forming a liner with a thread having a spherical profile thread crest and a shell with a shell thread engageable with the liner thread.

In another aspect of the invention, a method of attaching an acetabular liner to an acetabular shell includes providing a liner with a liner thread having a spherical profile thread crest and threading it into a shell with a shell thread engageable with the liner thread.

BRIEF DESCRIPTION OF THE DRAWINGS

Various embodiments of the present invention will be discussed with reference to the appended drawings. These drawings depict only illustrative embodiments of the invention and are not to be considered limiting of its scope.

FIG. 1 is an exploded perspective view of a modular acetabular cup assembly according to the present invention;

FIG. 2 is a side sectional view of the assembly of FIG. 1 in combination with additional total hip replacement components;

FIG. 3 is a detail view taken from FIG. 2;

DESCRIPTION OF THE ILLUSTRATED EMBODIMENTS

Figure 4:
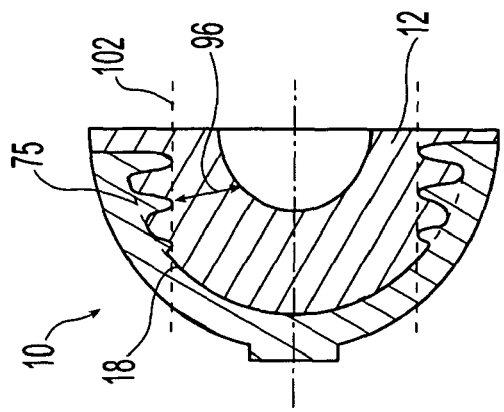
FIG. 4 is a side sectional view of the assembly of FIG. 1 illustrating an optional thread configuration.

Embodiments of an acetabular cup assembly include a shell component, a liner component, and a mechanism for retaining the liner in the shell including a spherical profile thread spiraling around a portion of each of the shell and liner. This mechanism may be provided with just two components, each having a unitary construction, to minimize the number of parts in the assembly.

Each of the liner and shell may have a thread crest and a thread root. The thread crest of the liner mates with the thread root of the shell. The thread crest, the thread root, or both may have a spherical profile. For example, the liner may have a hemispherical back forming a spherical profile thread root and a spherical profile thread crest projecting from the back and spiraling around the back. In this example, the shell would have a corresponding spherical profile thread crest and root for engagement with the liner thread. Alternatively, one of the root or crest of the thread may have another profile such as conical, cylindrical, or other suitable profile.

The liner and shell may include self-locking threads in which a portion of the threads interfere with one another to cause a binding engagement. For example, a portion of the shell thread profile may differ in dimension from a corresponding portion of the liner thread profile such that upon screwing of the liner into the shell the portions interfere with one another. The portions may differ in one or more of the dimensions of pitch, diameter, thread angle, or other suitable dimension.

The threads may be configured so that the shell and liner have a uniform thickness or they may be configured to provide a gradient thickness. For example, the threads may be configured so that the liner is thicker in a polar region and the shell is thicker in a rim region.

FIGS. 1–3 depict an illustrative embodiment of an acetabular cup assembly 10 and its placement in a human hip joint with additional mating implants. The acetabular cup assembly 10 includes a liner 12 for articulating engagement with a femoral component 56 and a shell 14 for securing the liner 12 in a hemispherical acetabulum 50 in the pelvis 52.

The liner 12 includes a generally hemispherical body having a substantially planar face 16 and a convex back 18. A raised lip may be formed adjacent the face 16 as is commonly provided with constrained acetabular liners. The convex back 18 terminates at a polar region 20. A hemispherical concave bearing surface 22 extends into the body through the face 16 toward the polar region 20. A liner screw thread 23 spirals around the back 18 of the liner 12 to secure the liner 12 within the shell 14. The liner screw thread 23 decreases in diameter from near the face 16 toward the polar region 20. The liner screw thread 23 includes a thread crest 24 and a thread root 26. In the illustrative embodiment of FIGS. 1–3, the liner thread root 26 coincides with the convex back 18 of the liner 12 and has a spherical profile. The liner thread crest 24 is raised above the back 18 and also has a spherical profile 28. Notches 30 around the face 16 permit a tool to grip the liner 12 and rotate it into the shell 14.

The shell 14 includes a hollow hemispherical body 32 having an exterior surface 33 with an opening 34 near the equator 36 and terminating at a polar region 38 opposite the opening 34. The interior surface 40 of the shell 14 is hemispherical to receive the back 18 of the liner 12. A shell screw thread 42 spirals into the body 32 from near the opening 34 toward the polar region 38. The shell screw thread 42 includes a shell thread crest 44 and a thread root 46. In the illustrative embodiment of FIGS. 1–3, the shell thread crest 44 coincides with the interior surface 40 of the shell 14 and has a spherical profile. The shell thread root 46 is formed into the interior surface 40 and also has a spherical profile 28. The shell 14 body 32 may have pores or other bone growth or cement receiving features on the exterior surface 33 to enhance its fixation in the acetabulum 50.

The illustrative liner 12 and shell 14 may be made by a variety of forming processes including machining, casting, forging, compression molding, injection molding, sintering, and/or other suitable processes. The illustrative liner 12 and shell 14 may be made of a variety of materials including metal, polymer, ceramic, and/or other suitable materials. For example, the liner 12 may be made of polyethylene and the shell 14 from a metal such as cobalt chromium alloy. In this example, the shell screw thread 42 may form an interference fit with the liner screw thread 23 such that the polyethylene of the liner 12 is deformed and the liner 12 and shell 14 fit closely together. Furthermore, because of the differing expansion coefficients of metal and polyethylene, the liner 12 will expand more than the shell 14 when the assembly 10 is warmed by the patient's body. This differential expansion will further lock the shell screw threads 42 and the liner screw threads 23 to resist relative motion between them. As another example, the liner 12 and shell 14 may both be made of metal such that the liner screw threads 23 and shell screw threads 42 may be tightened into rigid locking arrangement. The liner 12 and shell 14 may each be machined by programming a computer controlled machine tool to guide a cutter to follow a spherical profile to form the interior, exterior, thread crest and thread root of each component.

In use, the acetabular cup assembly 10 lines the acetabulum 50 on the pelvic side of the hip joint. The liner 12 is screwed into the shell 14 to wedge the components tightly together. The acetabular cup assembly 10 is then pressed into the prepared acetabulum 50 of the pelvis 52. The shell 14 may abut the bone or a layer of bone cement 54 may be positioned between the acetabulum 50 and the shell 14 to lock the assembly 10 in place. A femoral prosthesis 55 replaces the natural femoral head. The femoral prosthesis includes a stem component 56 and an articulating head component 58. The femoral stem component 56 is seated in a prepared intramedullary space 60 of the femur 62. The femoral stem component 56 may abut the bone or a layer of bone cement 64 may be positioned between the bone and the femoral stem component 56. The articulating head component 58 may be permanently affixed to the femoral stem component 56 or it may be a modular piece fit on the femoral stem component 56 at the time of surgery. After the acetabular cup assembly 10 and femoral implants 56, 58 have been implanted, the head component 58 is inserted into the concave bearing surface 22 of the liner 12 to restore normal hip joint function.

FIG. 4–8 depict alternative thread configurations according to the invention. FIG. 4 depicts a thread configuration in which the shell and liner thread crests and roots are both spherical similar to FIGS. 1–3. However, in the configuration of FIG. 4, the liner thread crest 70 coincides with the hemispherical back side 18 of the liner 12 and has a spherical profile 75. The liner thread root 72 is formed into the back side 18 of the liner 12 and also has a spherical profile 74. The shell thread root 76 coincides with the hemispherical interior surface 40 of the shell 14 and has a spherical profile 75. The shell thread crest 78 projects above the interior surface 40 of the shell 14 and also has a spherical profile 74. In both the embodiment of FIGS. 1–3 and the embodiment of FIG. 4, the shell 14 wall has a substantially uniform thickness 80 around the periphery of the shell 14. Likewise, the thickness 82 of the liner 12 is substantially uniform. This configuration thus permits screw thread locking of a hemispherical liner 12 into a hemispherical shell 14 while maintaining uniform liner 12 and shell 14 thicknesses.

Figure 5:
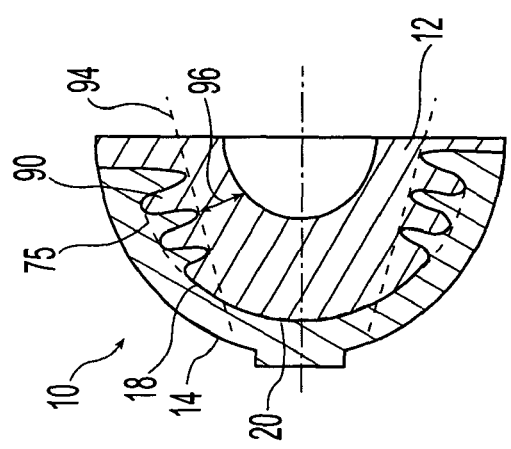
FIG. 5 is a side sectional view of the assembly of FIG. 1 illustrating an optional thread configuration.
Figure 6:
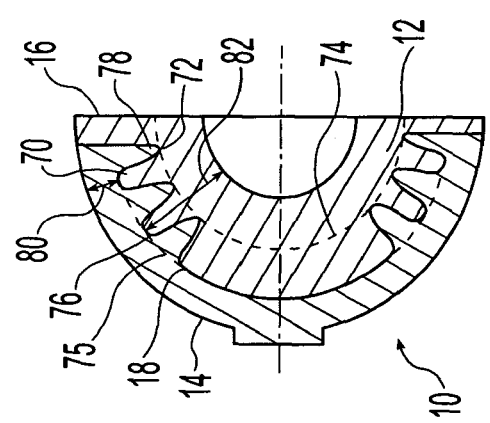
FIG. 6 is a side sectional view of the assembly of FIG. 1 illustrating an optional thread configuration.

FIG. 5 depicts a thread configuration in which the liner thread 90 has a spherical crest profile 75 and a conical root profile 94. In this configuration, the threads are shallower toward the polar region 20 of the liner 12 than they are toward the face 16 of the liner 12. Thus, the threads intrude less into the liner 12 near the polar region 20 leaving a thicker uninterrupted region 96 of the liner 12 toward the polar region 20. It is believed that this thicker region 96 provides more wear resistance in the more highly loaded portion of the liner 12. Likewise, it is believed that deeper thread engagement near the face 16 provides more resistance to separation of the liner 12 and shell 14 where separation forces are higher. FIG. 6 depicts a thread configuration similar to FIG. 5 but with a cylindrical liner thread root profile 102. This configuration has a similar, but more pronounced, effect as the configuration of FIG. 5. The uninterrupted region 96 of the liner 12 is proportionally larger than that of the configuration of FIG. 5. The liner thread configurations of FIGS. 5 and 6 may be formed by programming a computer controlled machine tool to guide a cutter to follow a spherical profile to form the liner thread crest profile 75. The liner thread root profiles 94, 102 may be formed by programming a computer controlled machine tool to guide a cutter to follow conical and cylindrical profiles respectively.

Figure 7:
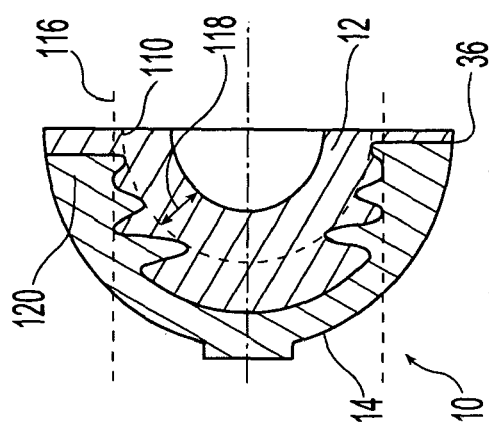
FIG. 7 is a side sectional view of the assembly of FIG. 1 illustrating an optional thread configuration.
Figure 8:
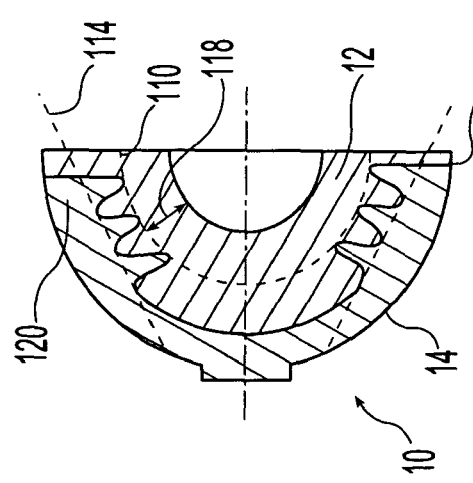
FIG. 8 is a side sectional view of the assembly of FIG. 1 illustrating an optional thread configuration.

FIGS. 7 and 8 depict thread configurations having spherical liner thread root profiles 110 and either conical 114 or cylindrical 116 liner thread crest profiles. These configurations permit a predetermined minimum uninterrupted liner thickness 118 while providing a thickened shell region 120 of the shell 14 wall near the equator 36 of the shell 14. Thus the shell 14 is strengthened near the equator 36 to resist hoop stresses caused by loading of the acetabular cup assembly 10 as may be desired in certain applications. The liner thread configurations of FIGS. 7 and 8 may be formed by programming a computer controlled machine tool to guide a cutter to follow a spherical profile to form the liner thread root profile 110. The liner thread crest profiles 114, 116 may be formed by programming a computer controlled machine tool to guide a cutter to follow conical and cylindrical profiles respectively.

Although embodiments of implants and their use have been described and illustrated in detail, it is to be understood that the same is intended by way of illustration and example only and is not to be taken by way of limitation. Accordingly, variations in and modifications to the implants and their use will be apparent to those of ordinary skill in the art, and the following claims are intended to cover all such modifications and equivalents.

What is claimed is:

1. A hip prosthesis comprising:
    an acetabular liner including a hemispherical convex back and a face opposite the hemispherical convex back, the hemispherical convex back defining a polar region, a concave bearing surface extending into the liner through the face toward the polar region, a screw thread spiraling around a portion of the hemispherical convex back, the screw thread having a thread crest and a thread root, the thread crest following a spherical profile as it spirals around the hemispherical convex back toward the polar region; and
    an acetabular shell including a hemispherical cavity for receiving the convex back the hemispherical cavity having a polar region, a screw thread spiraling around a portion of the cavity, the screw thread having a thread root following a spherical profile as it spirals around the cavity toward the polar region, the thread root being engageable with the thread crest of the liner screw thread.

2. The hip prosthesis of claim 1 wherein the liner thread root is coincident with the hemispherical convex back and the liner thread crest projects beyond the hemispherical convex back and follows a spherical profile spaced from the spherical convex back.

3. The hip prosthesis of claim 1 wherein the liner thread comprises a conical profile thread root and the acetabular shell cavity thread comprises a corresponding conical profile thread crest.

4. The hip prosthesis of claim 1 wherein the liner thread comprises a cylindrical profile thread root and the acetabular shell cavity thread comprises a corresponding cylindrical profile thread crest.

5. The hip prosthesis of claim 1 wherein the liner thread crest spirals-over most of the hemispherical convex back between the face and the polar region.

6. The hip prosthesis of claim 5 wherein the liner thread and shell thread comprise a self-locking arrangement in which a portion of the shell thread profile differs in a dimension from a corresponding portion of the liner thread profile, the shell thread and liner thread defining a self-locking thread interference.

7. The hip prosthesis of claim 1 further comprising a femoral prosthesis including a stem portion and a head portion, the head portion being matingly engageable with the concave bearing surface of the acetabular liner.

8. The hip prosthesis of claim 1 further comprising bone cement positionable between the shell and acetabulum to fix the shell in the acetabulum.

9. The hip prosthesis of claim 1 wherein, the liner thread crest is coincident with the spherical convex back and the liner thread root extends into the spherical convex back and follows a spherical profile spaced from the spherical convex back.

10. A hip prosthesis comprising:
    an acetabular liner including a hemispherical convex back and a face opposite the hemispherical convex back, the hemispherical convex back defining a polar region, a concave bearing surface extending into the liner through the face toward the polar region, a screw thread spiraling around a portion of the convex back, the screw thread having a thread crest and a thread root, the thread root following a spherical profile as it spirals around the hemispherical convex back toward the polar region; and
    an acetabular shell including a hemispherical cavity for receiving the hemispherical convex back, a screw thread spiraling around a portion of the cavity, the hemispherical cavity having a polar region, the screw thread having a thread crest following a spherical profile as it spirals around the cavity toward the polar region, the thread crest being engageable with the thread root of the liner screw thread.

11. The hip prosthesis of claim 10 wherein the liner thread comprises a conical profile thread crest.

12. The hip prosthesis of claim 10 wherein the liner thread comprises a cylindrical profile thread crest.

* * * * *

UNITED STATES PATENT AND TRADEMARK OFFICE
CERTIFICATE OF CORRECTION

| | |
|---|---|
| PATENT NO. | : 7,044,974 B2 |
| APPLICATION NO. | : 10/649567 |
| DATED | : May 16, 2006 |
| INVENTOR(S) | : Frank D. Garber and John P. Horn |

It is certified that error appears in the above-identified patent and that said Letters Patent is hereby corrected as shown below:

Title page, [75]
The second inventor's name has been misspelled.
"John P. Hom" should read --John P. Horn--

Signed and Sealed this

Third Day of October, 2006

JON W. DUDAS
*Director of the United States Patent and Trademark Office*